US008961010B2

(12) United States Patent
Meyer et al.

(10) Patent No.: US 8,961,010 B2
(45) Date of Patent: Feb. 24, 2015

(54) C-ARM X-RAY SYSTEM AND METHOD OF COMPENSATION FOR C-ARM DEFORMATIONS AND OSCILLATIONS

(71) Applicants: Michael Meyer, Hausen (DE); Nenad Pavlovic, Erlangen (DE)

(72) Inventors: Michael Meyer, Hausen (DE); Nenad Pavlovic, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 191 days.

(21) Appl. No.: 13/761,970

(22) Filed: Feb. 7, 2013

(65) Prior Publication Data

US 2013/0202093 A1 Aug. 8, 2013

(30) Foreign Application Priority Data

Feb. 8, 2012 (DE) ........................ 10 2012 201 857

(51) Int. Cl.
*H05G 1/02* (2006.01)
*A61B 6/00* (2006.01)

(52) U.S. Cl.
CPC ................ *H05G 1/02* (2013.01); *A61B 6/4441* (2013.01); *A61B 6/547* (2013.01); *A61B 6/588* (2013.01)
USPC ........................................................ 378/197

(58) Field of Classification Search
CPC ....... A61B 6/4441; A61B 6/4464; H05G 1/02
USPC ................................................ 378/193–197
See application file for complete search history.

(56) References Cited

U.S. PATENT DOCUMENTS 7,874,727 B2 1/2011 Forster et al.
7,905,658 B2 3/2011 Groβ et al.
2005/0063510 A1* 3/2005 Hieronimi et al. .............. 378/65
2012/0236999 A1 9/2012 Altvater et al.

FOREIGN PATENT DOCUMENTS

DE 101 61 152 A1 6/2003
DE 10 2005 018 326 A1 11/2006
DE 10 2008 003 815 A1 7/2009
DE 10 2011 005 492 A1 9/2012

OTHER PUBLICATIONS

German Office Action dated Oct. 16, 2012 for corresponding German Patent Application No. DE 10 2012 201 857.3 with English translation.

* cited by examiner

*Primary Examiner* — Courtney Thomas
(74) *Attorney, Agent, or Firm* — Lempia Summerfield Katz LLC

(57) ABSTRACT

An x-ray system having a C-arm 1 and an associated method are provided. The x-ray system includes at least one adjustment unit for at least one component of the x-ray system that is actively connected to the C-arm. The at least one adjustment unit compensates for a spatial change in position of the component caused by deformation and/or oscillation of the C-arm.

20 Claims, 3 Drawing Sheets

C-ARM X-RAY SYSTEM AND METHOD OF COMPENSATION FOR C-ARM DEFORMATIONS AND OSCILLATIONS

This application claims the benefit of DE 10 2012 201 857.3, filed on Feb. 8, 2012, which is hereby incorporated by reference.

BACKGROUND

The present embodiments relate to an x-ray system having a C-arm and a method for compensating for a deformation and/or oscillation of a C-arm.

The C-arm of an x-ray system is loaded by the dead weight of components fastened to the C-arm (e.g., an x-ray emitter, a detector, a diaphragm and a grid). On account of a finite rigidity of the C-arm, the C-arm is deformed by the dead weights. The C-arm may also oscillate in its entirety due to dynamic loads. Several problems are caused as a result.

The components move toward one another on account of static deformations of the C-arm, which, particularly in 3D reconstructions, results in a falsification of the x-ray image recordings. Dynamic loads on account of inertia forces result in unwanted oscillations of the C-arm, as a result of which the alignment relative to the isocenter is disturbed. The use of innovative components such as, for example, a high focusing grid that requires a very precise alignment is hampered. Oscillations occur on account of the finite rigidity of the C-arm. The oscillations have a negative affect on the image quality and the examination time. These effects are very disruptive (e.g., in the case of a C-arm angiography system).

It is known from the prior art to improve the rigidity of the C-arm by the geometry of the C-arm being optimized. Attempts are made to keep the deformations as low as possible in all directions by a larger cross-section of the C-arm. Solutions of this type result in the C-arm becoming larger and heavier, thereby causing problems. The weight of the C-arm is increased by a larger cross-section, as a result of which the dynamics of the C-arm movement is negatively affected. Both the maximum speed and the acceleration are reduced. The available space reduces on account of the larger cross-section with an identical C-arm length, as a result of which the accessibility in terms of the patient worsens with specific examinations. The fitting of heavy components requires an even larger cross-section of the C-arm, as a result of which the weight is increased again. An upper limit is imposed in terms of optimization of the cross-section.

With known x-ray devices such as disclosed, for example, in DE 10 2008 003 815 A1, the C-arm is arranged on a stand that is, for example, vertical on the base side and may be rotated about a usually horizontal axis via a swivel guide. In the swivel guide, the C-arm is rotatable about an isocenter along an arc-shaped guiding path of the C-arm. A particularly light C-arm is to be used in order to achieve the best possible dynamics in applications, in which the C-arm is moved with significant speed along the swivel guide. An angiography x-ray device is an example. For this reason, C-arms made of extruded sections that include a rectangular hollow profile in cross-section may be used.

Instead of a floor stand and connecting the C-arm via the swivel guide, as a result of which the required degrees of movement freedom for the C-arm movement and positioning is realized, it is known to arrange the C-arm on an industrial robot with a robot arm and a corresponding control device. With such an embodiment, the degrees of freedom are provided by the six axes of movement of the robot. The C-arm is rotationally mounted directly on the robot arm.

DE 10 2005 018 326 A1 discloses the creation of a sharp x-ray image using an x-ray emitter or x-ray receiver that may be moved with respect to a holding position by a drive device despite a system structure that may be made to oscillate using a resonant frequency that is dependent on the respective holding position. In this process, at least one variable dependent on the respective holding position and relevant to the resonant frequency is detected. A desired movement control that counteracts the oscillation is determined in order to achieve a movement state of the x-ray emitter or x-ray receiver provided for the x-ray examination as a function of the at least one respective variable and the movement of the x-ray emitter, or the x-ray receiver is controlled by the drive device in accordance with the desired movement control.

DE 10 2011 005 492 A1 describes an x-ray apparatus with a C-arm, on which an x-ray source and an x-ray detector may be attached in the opposite arrangement, at least one actuator for positioning the C-arm relative to a mounting facility, and a control device for controlling the actuator. The x-ray apparatus includes at least one sensor that, at a first position of the C-arm, detects a deformation of the C-arm and transforms the deformation into an output signal. The deformation of the C-arm may be influenced by a force exerted by an operator and directly or indirectly affecting a second position on the C-arm. The control device influences the actuator as a function of the output signal of the sensor.

DE 101 61 152 A1 discloses a radiation therapy system having a hexapod unit, on which a collimator is arranged.

SUMMARY AND DESCRIPTION

The present embodiments may obviate one or more of the drawbacks or limitations in the related art. For example, an x-ray system having a C-arm and an associated method that compensate for deformations and oscillations of the C-arm without changing the cross-section of the C-arm is provided.

The deformations (e.g., warping) and oscillations of a C-arm are permissible, because these are mechanically compensated for by adjustment units.

An x-ray system having a C-arm with at least one adjustment unit for at least one component of the x-ray system that is mechanically connected to the C-arm by the adjustment unit. The component compensates for a spatial change in position of the component caused by deformation and/or oscillation of the C-arm. The component is an x-ray emitter, an x-ray detector, an x-ray beam diaphragm or an x-ray grid. "Falsifications" of x-ray images caused by deformation of the C-arm are minimized or eliminated, such that applications with components aligned precisely with one another are enabled.

The deformation and/or oscillation by the dead weight of the component and/or by the rotational movement (e.g., by acceleration and braking) of the C-arm may also occur. The adjustment unit may include one to six degrees of freedom of movement.

In one development of the x-ray system, the adjustment unit may include a hexapod unit. A hexopod unit may include six legs, with two ends being held in a hinge in each instance. The hexapod unit stands on three points.

The x-ray system may further include at least one measuring unit that determines the spatial change in position. The measuring unit is, for example, a laser measuring unit.

The x-ray system may also include at least one control unit that actuates the adjustment unit such that the adjustment unit compensates for the spatial change in position of the components caused by deformation and/or oscillation of the C-arm.

In one embodiment, a method for compensating for a deformation and/or oscillation of a C-arm of an x-ray system is provided. A spatial change in position of the component caused by deformation and/or oscillation of the C-arm is mechanically compensated for by an adjustment unit arranged between the c-arm and a component of the x-ray system.

In a development of the method, the movements of the adjustment unit to compensate for the change in position may be determined in advance as a function of a C-arm position.

The movements of the adjustment unit in order to compensate for the change in position may also be implemented continuously during operation of the x-ray system. The adjustment thus takes place "online" without analytical description and/or measurements of the changes in position having taken place beforehand.

In a development of the method, the movements of the adjustment unit may be determined from a determination of a change in position.

The change in position may also be determined from the position of the component compared with a reference point or compared with a further component.

DETAILED DESCRIPTION OF THE DRAWINGS

Figure 1:
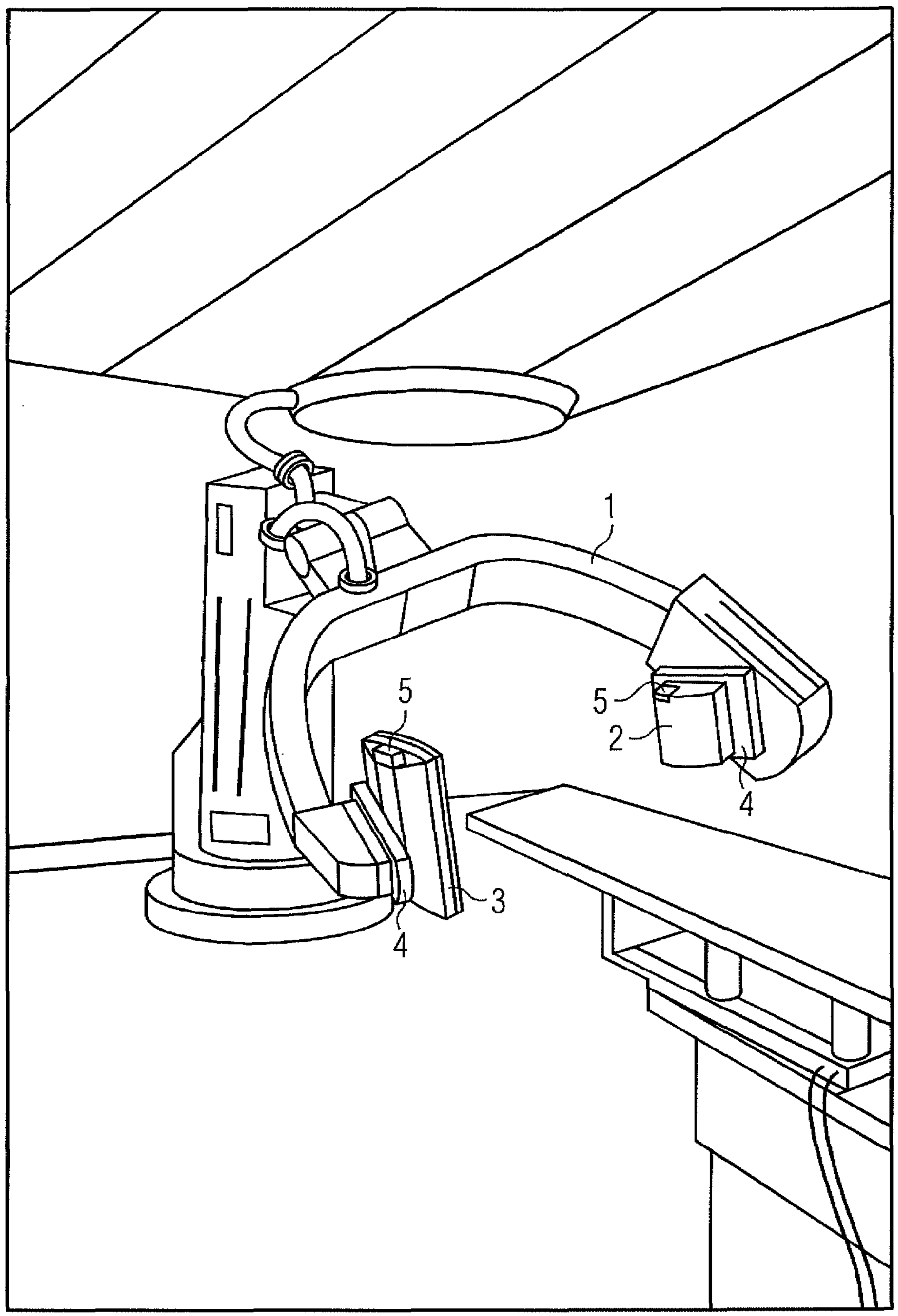
FIG. 1 shows a spatial view of one embodiment of a C-arm angiography system with adjustment units.

FIG. 1 shows one embodiment of an angiography system with a C-arm 1. An x-ray emitter 2 is disposed at one end of the C-arm 1, and an x-ray detector 3 is disposed at the other end. An adjustment unit 4 is arranged between the C-arm 1 and the x-ray emitter 2 and/or the x-ray detector 3. Unwanted changes in position of the x-ray emitter 2 and the x-ray detector 3 caused by deformations and/or oscillations of the C-arm 1 may be compensated for with the aid of the adjustment units 4. Measuring units 5 (e.g., laser displacement sensors) are arranged on the x-ray emitter 2 and the x-ray detector 3 in order to measure the changes in position. The adjustment units 5 are actuated for the purpose of compensation movements using a control unit (not shown).

Figure 2:
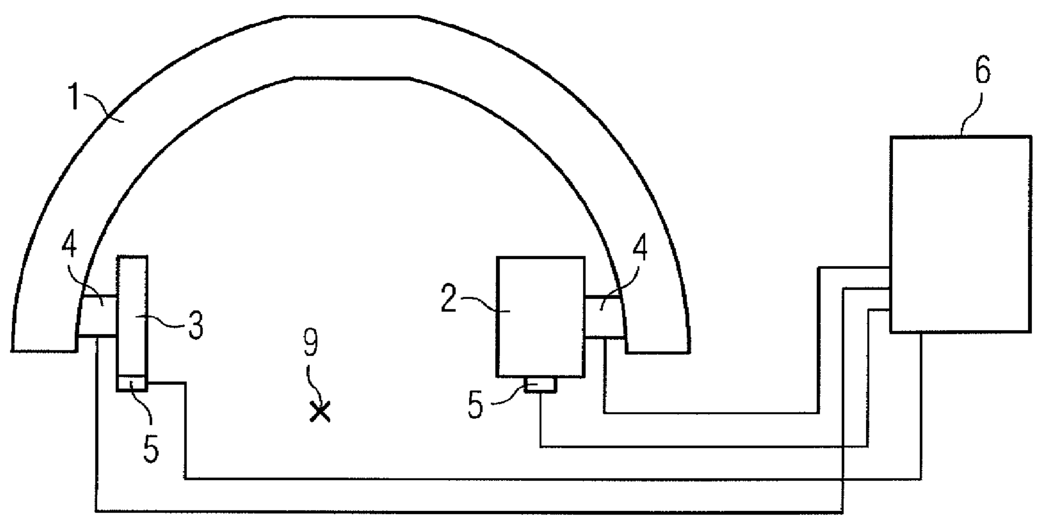
FIG. 2 shows a block diagram of one embodiment of an x-ray system with adjustment units.

FIG. 2 shows a block diagram of one embodiment of an x-ray system having a C-arm 1. Components (e.g., an x-ray emitter 2 and an x-ray detector 3) are arranged at the ends of the C-arm 1. The components 2, 3 are fastened to the C-arm 1 by an adjustment unit 4 in each instance. With the aid of the adjustment unit 4, changes in position of the components 2, 3 caused by a deformation (e.g., a distortion and/or oscillation of the C-arm 1) may be compensated for. The unwanted changes in position are determined with the aid of measuring units 5 arranged on the components 2, 3. The compensation movements of the adjustment units 4 are controlled via a control unit 6. This thus provides that the components 2, 3 have the correct position relative to one another irrespective of the deformations of the C-arm 1.

This provides that the problem of deformations and/or oscillations is solved by an adaptive (dynamic) compensation for the C-arm deformations and C-arm oscillations. The components 2, 3 are positioned by the adjustment units 4 as a function of the current position of the C-arm 1, such that during a clinical examination, the relative and/or absolute position of the components 2, 3 remain unchanged relative to one another. The change in position may be determined compared with a reference point 9 or compared with other components.

In one embodiment of the method of compensation for the deformation and/or oscillation, the movement of the adjustment units 4 is controlled. The compensation movements of the adjustment units 4 to compensate for deformation and oscillation are determined prior to the clinical application, and the adjustment units 4 are actuated based hereupon during an examination. The compensation movements may be described analytically for the entire movement space. Compensation movements may also be determined in different positions of the C-arm 1, and the values in the "intermediate layers" are interpolated. There are two variants here.

With the "Teach-in method," the adjustment units 4 are guided with the control unit 6 into the desired position. The ranges and angles determined in this way for the adjustment units 4 are stored in the control unit 6. This act is repeated until all desired positions of the C-arm 1 are traversed. The program sequence includes, in the adjustment units 4, automatically executing all stored movements in corresponding positions of the C-arm 1 during the clinical examination. The adjustment movements in the "intermediate positions" are determined by interpolation.

When monitoring the relative position between the components 2, 3, the parallelism and the distance between the components 2, 3 and the centering of the components 2, 3 are monitored with respect to one another. The parallelism and the distance may be monitored with the aid of three laser travel sensors. The distance between the components 2, 3 is measured at three points, and the deviation from the desired distance is determined therefrom. The tilt of the components 2,3 relative to one another may also be determined with the aid of this data. In order to monitor the centering, three markers may be attached to the components facing the lasers, for example. These markers are to be "hit" by the lasers through the compensation movements.

With the "playback method," the adjustment units 4 are brought into selected positions of the C-arm 1 by direct guiding by a user into the desired position. The x-ray system then repeats these movements automatically during clinical examinations. The adjustment based on this principle may be used exclusively in the positions of the C-arm 1, in which the movement was executed by hand. An interpolation for the intermediate positions may not be provided. This method may accordingly be applied exclusively to 2D images in specific positions. In order to enable the 3D reconstruction, mobile coordinate measuring systems may be applied to the components to be traced. Therefore, during the component control, the coordinates may be registered and calculated in the required ranges and/or angles. The compensation movements of the adjustment units 4 for the "intermediate positions" of the C-arm 1 may be interpolated on this basis. The relative position of the components relative to one another is monitored as in the teach-in method.

In one embodiment, the movement of the adjustment units is regulated "online". In this case, the relative position of the components is largely monitored during the travel of the C-arm 1. On this basis, the movement of the adjustment units 4 is regulated during a clinical examination. The current relative position of the components 2, 3 may be determined directly or indirectly. When the position is determined directly, for example, the parallelism between the components 2, 3 is monitored by distance measurements. This is more complicated because additional measuring units (e.g., lasers) that are to be fastened to the components 2, 3 may be used. An indirect position is determined by measuring the C-arm twistings and/or oscillations (e.g., by expansion measuring strips and/or acceleration sensors), and the components 2, 3 are adjusted based on the measured values.

As a function of the deformations and oscillations to be compensated for, the adjustment units 4 may include one or more translational and/or rotational degrees of freedom (e.g., overall a maximum of six). The adjustment units 4 may include a number of actuators or motors and different serial/parallel kinematics.

Figure 3:
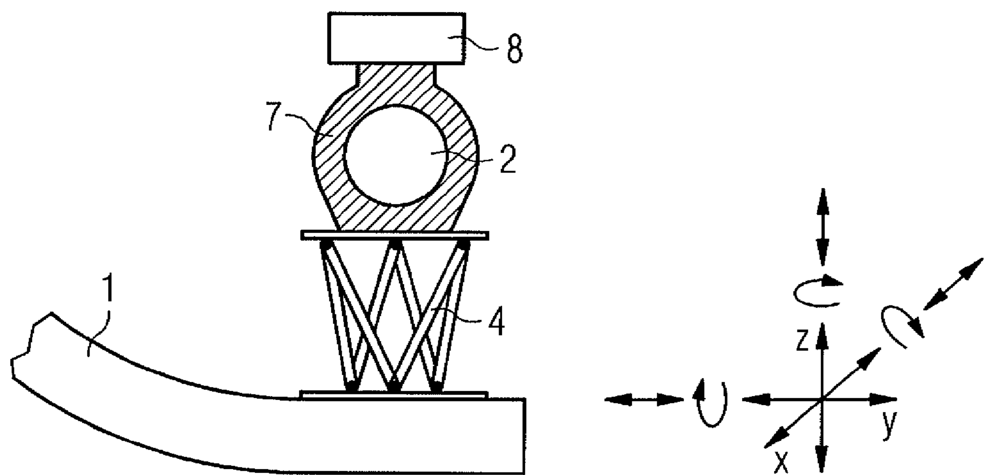
FIG. 3 shows a side view of one embodiment of a C-arm having an adjustment unit connected to an x-ray emitter.

FIG. 3 shows an example of an adjustment unit 4 arranged on a C-arm 1. The adjustment unit 4 is embodied as a hexapod. An x-ray emitter 2 and diaphragm 8 are mechanically connected to the adjustment unit 4 by an adapter 7. Movement (e.g., rotation, translation) of the adjustment unit 4 with six degrees of freedom along the three axes x, y, z compensates for any deformation and/or oscillation of the C-arm 1.

Figure 4:
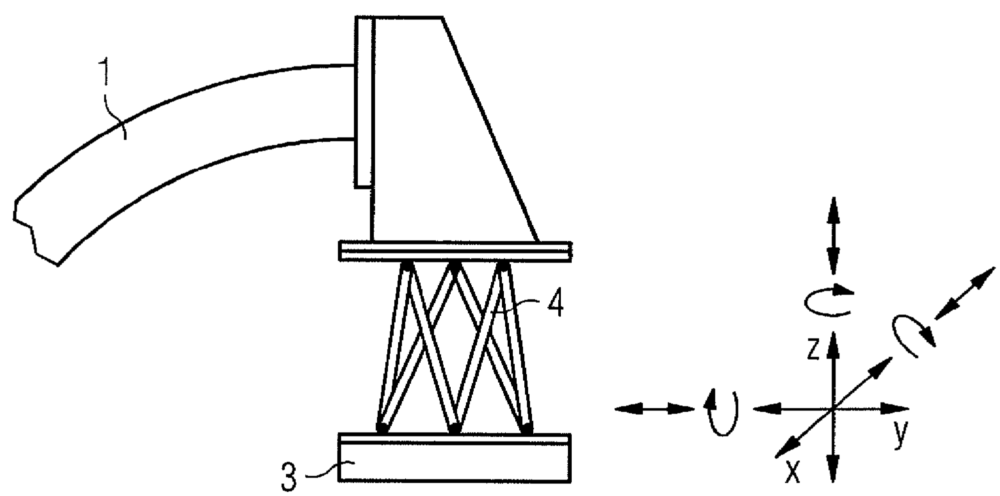
FIG. 4 shows a side view of one embodiment of a C-arm having an adjustment unit connected to a detector.

FIG. 4 shows a further example of an adjustment unit 4 arranged on a C-arm 1. The adjustment unit 4 is embodied as a hexapod. An x-ray detector 3 and grid is connected to the adjustment unit 4 by an adapter 7. Movement (e.g., rotation, translation) of the adjustment unit 4 with six degrees of freedom along the three axes x, y, z enables any deformation and/or oscillation of the C-arm 1 to be compensated for.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An x-ray system comprising:

a C-arm comprising:

at least one adjustment unit that is arranged between a component of the x-ray system and the C-arm and connects the component to the C-arm in a mechanically moveable manner, wherein the at least one adjustment unit is operable to compensate for a spatial change in position of the component caused by deformation, oscillation, or deformation and oscillation of the C-arm, and wherein the component comprises an x-ray emitter, an x-ray detector, an x-ray beam diaphragm, or an x-ray grid.

2. The x-ray system as claimed in claim 1, wherein the deformation, the oscillation, or the deformation and the oscillation occur on account of dead weight of the component, on account of a rotational movement of the C-arm, or a combination thereof.

3. The x-ray system as claimed in claim 2, wherein the rotational movement is rotational movement on account of acceleration and braking of the C-arm.

4. The x-ray system as claimed in claim 1, wherein the at least one adjustment unit has one to six degrees of freedom.

5. The x-ray system as claimed in claim 4, wherein the at least one adjustment unit comprises a hexapod unit.

6. The x-ray system as claimed in claim 1, further comprising at least one measuring unit operable to determine a spatial change in position.

7. The x-ray system as claimed in claim 1, further comprising at least one control unit operable to control the at least one adjustment unit such that the at least one adjustment unit compensates for a spatial change in position of the component caused by the deformation or the oscillation of the C-arm.

8. The x-ray system as claimed in claim 2, wherein the at least one adjustment unit has one to six degrees of freedom.

9. The x-ray system as claimed in claim 8, wherein the at least one adjustment unit comprises a hexapod unit.

10. The x-ray system as claimed in claim 2, further comprising at least one measuring unit operable to determine a spatial change in position.

11. The x-ray system as claimed in claim 5, further comprising at least one measuring unit operable to determine a spatial change in position.

12. The x-ray system as claimed in claim 2, further comprising at least one control unit operable to control the at least one adjustment unit such that the at least one adjustment unit compensates for a spatial change in position of the component caused by the deformation or the oscillation of the C-arm.

13. The x-ray system as claimed in claim 5, further comprising at least one control unit operable to control the at least one adjustment unit such that the at least one adjustment unit compensates for a spatial change in position of the component caused by the deformation or the oscillation of the C-arm.

14. The x-ray system as claimed in claim 6, further comprising at least one control unit operable to control the at least one adjustment unit such that the at least one adjustment unit compensates for a spatial change in position of the component caused by the deformation or the oscillation of the C-arm.

15. A method for compensating for a deformation or oscillation of a C-arm of an x-ray system, the method comprising:

compensating for a spatial change in position of components caused by deformation, oscillation, or deformation and oscillation of the C-arm by an adjustment unit that is arranged so as to be mechanically moveable between the C-arm and one of the components of the x-ray system, wherein the one component comprises an x-ray emitter, an x-ray detector, an x-ray beam diaphragm or an x-ray grid.

16. The method as claimed in claim 15, further comprising determining movements of the adjustment unit required to compensate for the change in position in advance as a function of positions of the C-arm.

17. The method as claimed in claim 16, wherein the movements of the adjustment unit required to compensate for the change in position are implemented continuously during operation of the x-ray system.

18. The method as claimed in claim 16, wherein the determining comprises determining from a determination of a change in position.

19. The method as claimed in claim 18, wherein the change in position is determined from a position of the component relative to a point of reference or relative to a further component.

20. The method as claimed in claim 17, wherein the determining comprises determining from a determination of a change in position.

* * * * *